(12) United States Patent
Pedrazzini

(10) Patent No.: US 8,147,778 B2
(45) Date of Patent: Apr. 3, 2012

(54) SPECIMEN CONTAINER CARRIER FOR CONVEYOR IN LABORATORY AUTOMATION SYSTEM

(75) Inventor: Gianandrea Pedrazzini, Paradiso (CH)

(73) Assignee: Inpeco IP Ltd., Valletta (MT)

(*) Notice: Subject to any disclaimer, the term of this patent is extended or adjusted under 35 U.S.C. 154(b) by 198 days.

(21) Appl. No.: 12/445,179

(22) PCT Filed: Oct. 11, 2006

(86) PCT No.: PCT/EP2006/067294
§ 371 (c)(1),
(2), (4) Date: Jul. 27, 2009

(87) PCT Pub. No.: WO2008/043394
PCT Pub. Date: Apr. 17, 2008

(65) Prior Publication Data
US 2010/0015007 A1    Jan. 21, 2010

(51) Int. Cl.
*B01L 9/06* (2006.01)
*G01N 35/04* (2006.01)
*G01N 35/10* (2006.01)

(52) U.S. Cl. .............. 422/562; 422/63; 422/65; 436/47; 436/48; 436/49; 206/443; 198/803.14; 198/867.12; 198/465.1

(58) Field of Classification Search .................... None
See application file for complete search history.

(56) References Cited

U.S. PATENT DOCUMENTS

| 5,014,868 | A | 5/1991 | Wittig et al. |
| 6,971,506 | B2 * | 12/2005 | Hassinen et al. ......... 198/803.14 |
| 2002/0040618 | A1 | 4/2002 | Dervaes |
| 2005/0037502 | A1 * | 2/2005 | Miller ............................ 436/43 |
| 2005/0271555 | A1 | 12/2005 | Itoh |

FOREIGN PATENT DOCUMENTS
EP    0 916 406 A2    5/1999

* cited by examiner

*Primary Examiner* — P. Kathryn Wright
(74) *Attorney, Agent, or Firm* — Birch, Stewart, Kolasch & Birch, LLP

(57) ABSTRACT

A specimen container carrier for a conveyor in a laboratory automation system which includes a circular body driven by the conveyor and container holding elements arranged in the circular body, the container holding elements being maintained in a container holding position by respective elastic elements and are connected to each other by synchronization elements forcing the specimen container to remain coaxially positioned with respect to the circular body.

2 Claims, 6 Drawing Sheets

SPECIMEN CONTAINER CARRIER FOR CONVEYOR IN LABORATORY AUTOMATION SYSTEM

The present invention concerns a specimen container carrier to be used for conveyor in laboratory automation systems.

In modern laboratory automation systems are settled a plurality of work stations for manipulating specimen containers.

As used herein, the term "specimen container" means an article that contains a solid or liquid and has a tubular opening for access of the contents, e.g., a test tube or vial.

Said work stations concern for example a decapper station, a capper station, an analysis station for the substance housed in the specimen container, a desealer station and similar.

The specimen containers are supported by detectable carriers which run, by a driven belt member, inside horizontal guides comprised in a transfer guiding unit.

Said transfer guiding unit connects the different work stations, and is provided with a plurality of detecting sensors which control the position of the carriers with their specimen containers.

The present invention is concerned with laboratory automation systems that make use of single specimen containers, in which each specimen container is associated with a respective carrier. This link is generated at the beginning of the laboratory operations, that is when specimen containers start their process.

Actually are known specimen container carriers constituted by a supporting circular body driven by the belt member of the conveyor, having a cavity which houses the specimen container.

Said specimen container is held in vertical position by a deformable gasket which is fixed on the throat of the cavity.

The deformability of the gasket allows to house specimen containers of different cross section.

This type of specimen container carrier present the following problems:
  the specimen container must be presented at any process spot perfectly, in repeatable position;
  the specimen container portion held by the carrier must be as limited as possible to allow access for the specimen container without compromising the holding capacity;
  the specimen container holding means should not hide the specimen container ID (barcode).

Object of the present invention is to provide a specimen container carrier which meets the above mentioned requirements.

According to the invention said object is achieved by a specimen container carrier for conveyor in laboratory automation systems, comprising a circular body driven by said conveyor and container holding means arranged in said circular body, characterized in that said container holding means are kept in a container holding position by respective elastic means and are connected to each other by synchronization means forcing the specimen container to remain coaxially positioned with respect to the circular body.

The synchronization means allows to distribute the elastic holding force exerted in the specimen container by said holding means.

The characteristics and advantages of the present invention will appear evident from the following detailed description of an embodiment thereof illustrated as non-limiting example in the enclosed drawings, in which.

Figure 1:
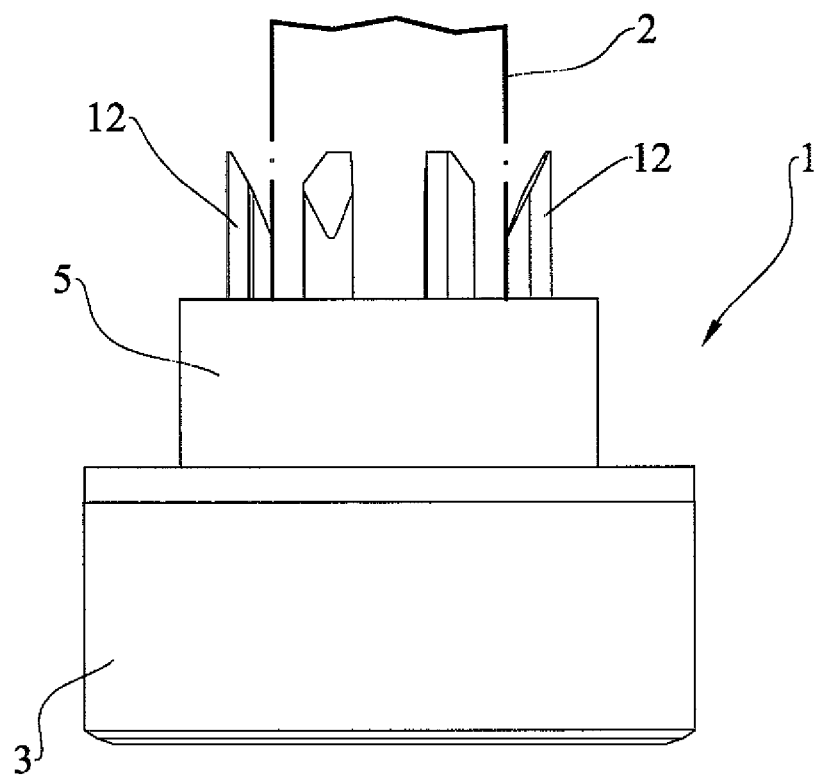
FIG. 1 is a lateral view of the specimen container carrier according to the present invention.

A carrier 1 for a specimen container 2 comprises a base circular body 3 with a cavity 4, and a closure member 5.

Figure 9:
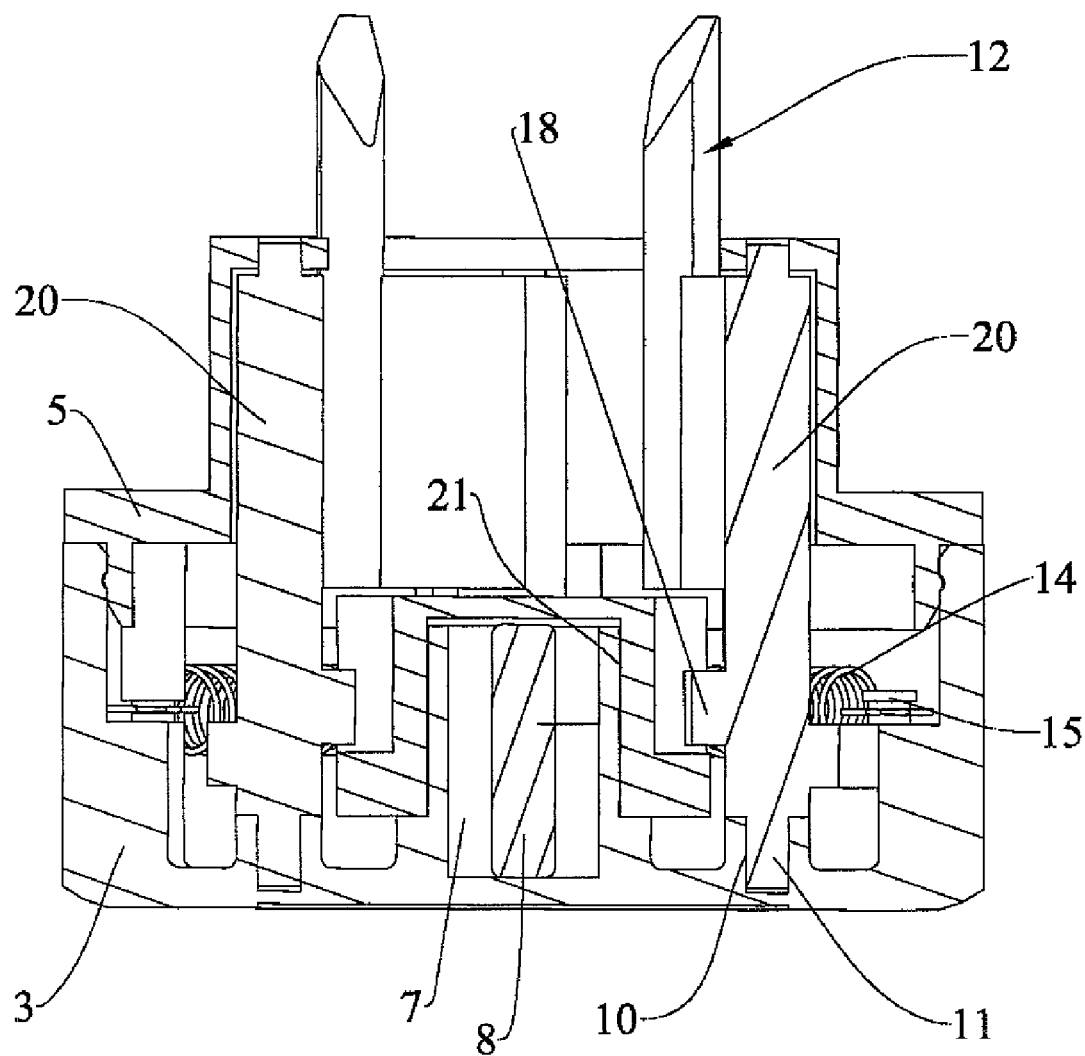
FIG. 9 is a sectional view according to line IX-IX of FIG. 2.

The base circular body 3 is provided with a central pin 6 with a cavity 7 in which an ID tag 8 is housed (FIG. 9).

Figure 5:
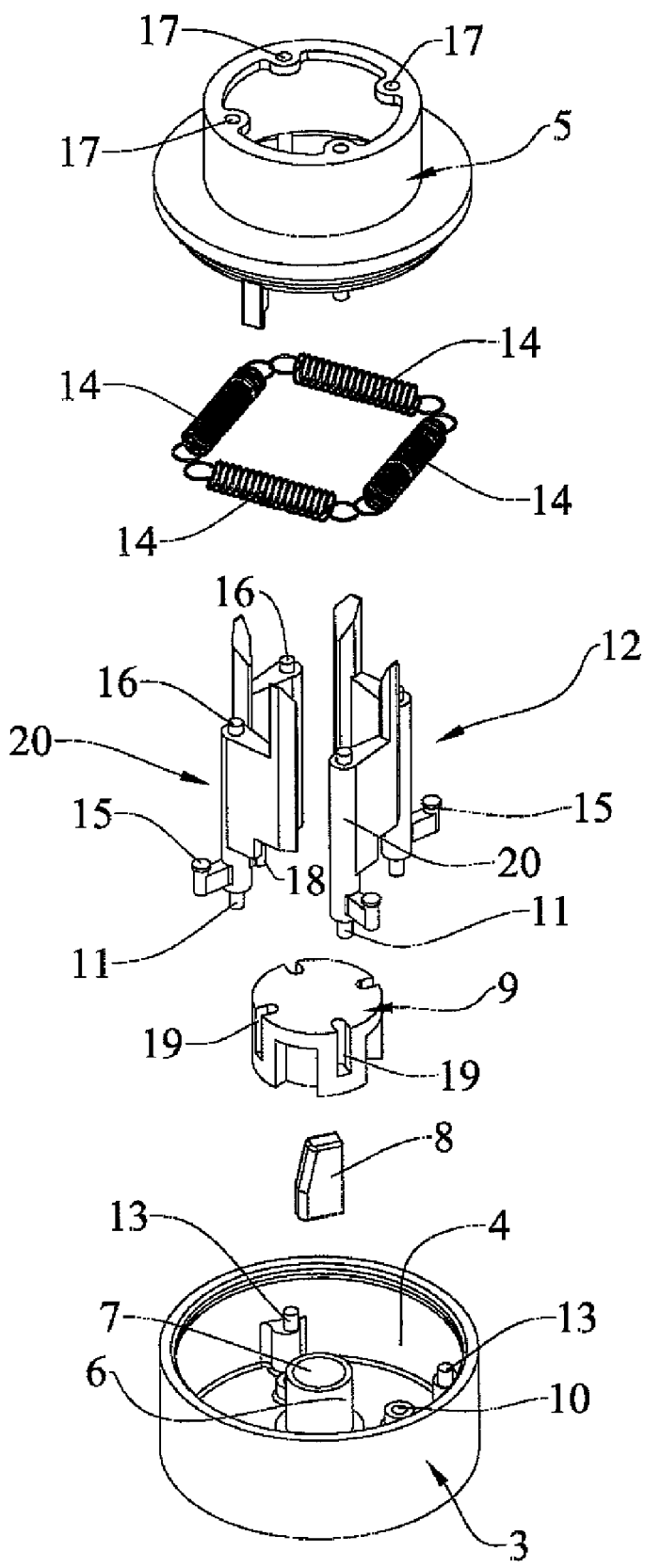
FIG. 5 is a perspective exploded view of the carrier specimen container.
Figure 8:
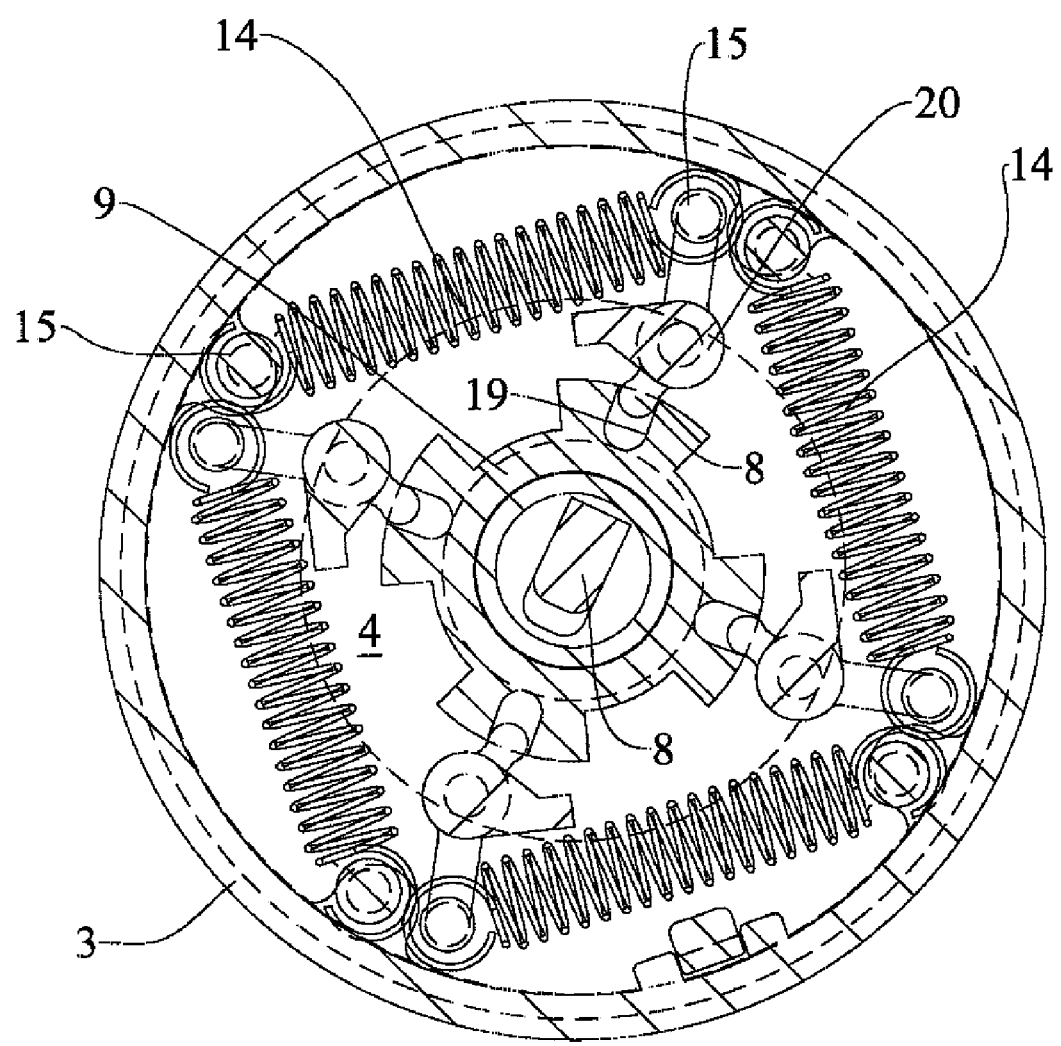
FIG. 8 is a sectional view according to line VIII-VIII of FIG. 3.

Said base circular body 3 is rotatably coupled with a synchronization rotor 9 with a cavity 21 which receives the pin 6, and is also provided with four pivoting coupling holes 10 for lower pivoting pintles or hinges 111 of four vertical centering fingers 12, and with spring coupling pintles 13 for the connection of four springs 14 further connected with spring coupling pintles 15 of the fingers 12 (FIGS. 5 and 8-9).

Figure 6:
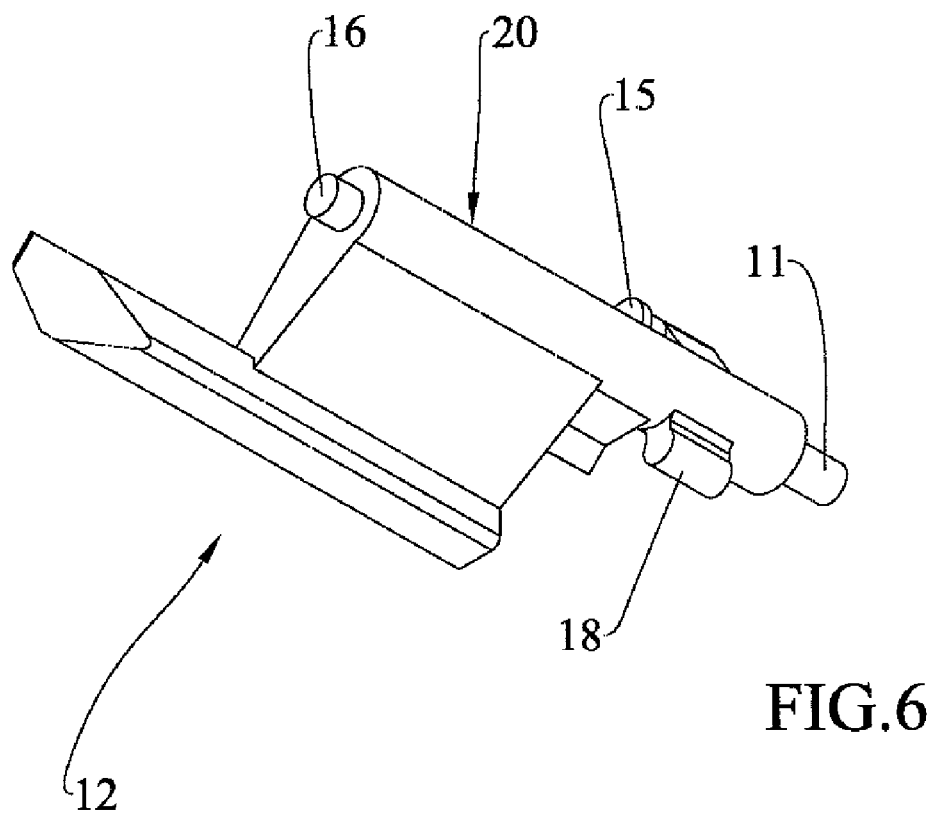
FIG. 6 is a perspective enlarged view of the holding means.
Figure 7:
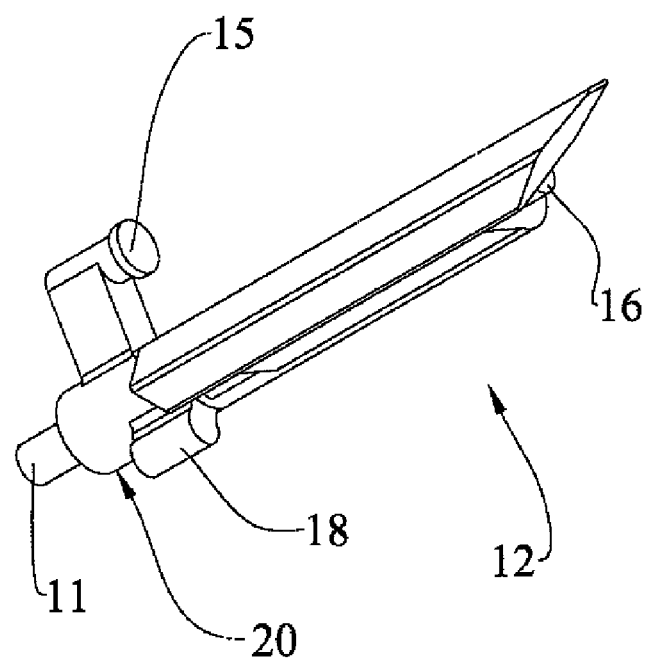
FIG. 7 is a further perspective enlarged view of the holding means.

The fingers 12 comprise upper pivoting pintles or hinges 16, which engage with pivoting coupling holes 17 of the closure member 5, and teeth 18 (FIGS. 6-8) which engage with slits 19 of the rotor 9.

Figure 4:
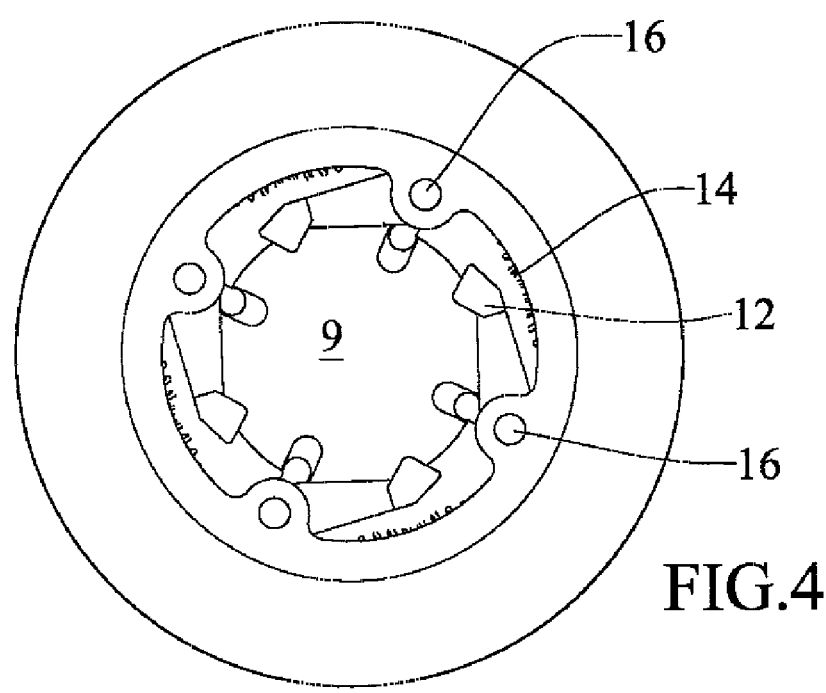
FIG. 4 is a top view of the specimen container carrier without the specimen container.

In FIG. 4 the fingers are shown in a rest position. The springs 14 push the fingers 12 around the pivot 20 towards (counterclockwise/inward rotation) the centre of the body 3.

Stop portions of the fingers 12 engage with the lateral wall of the rotor 9 to stop the inward rotation forced by the springs 14.

The rotor 9 synchronizes and balances the inward force of each finger 12.

Figure 2:
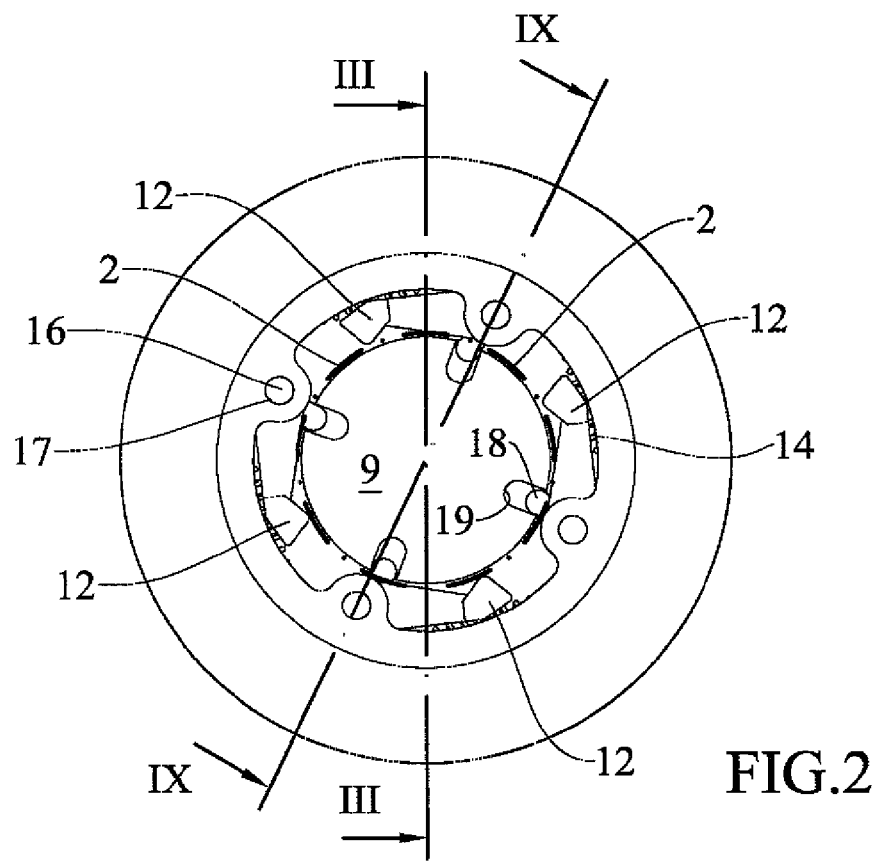
FIG. 2 is a top view of the specimen container carrier of FIG. 1.
Figure 3:
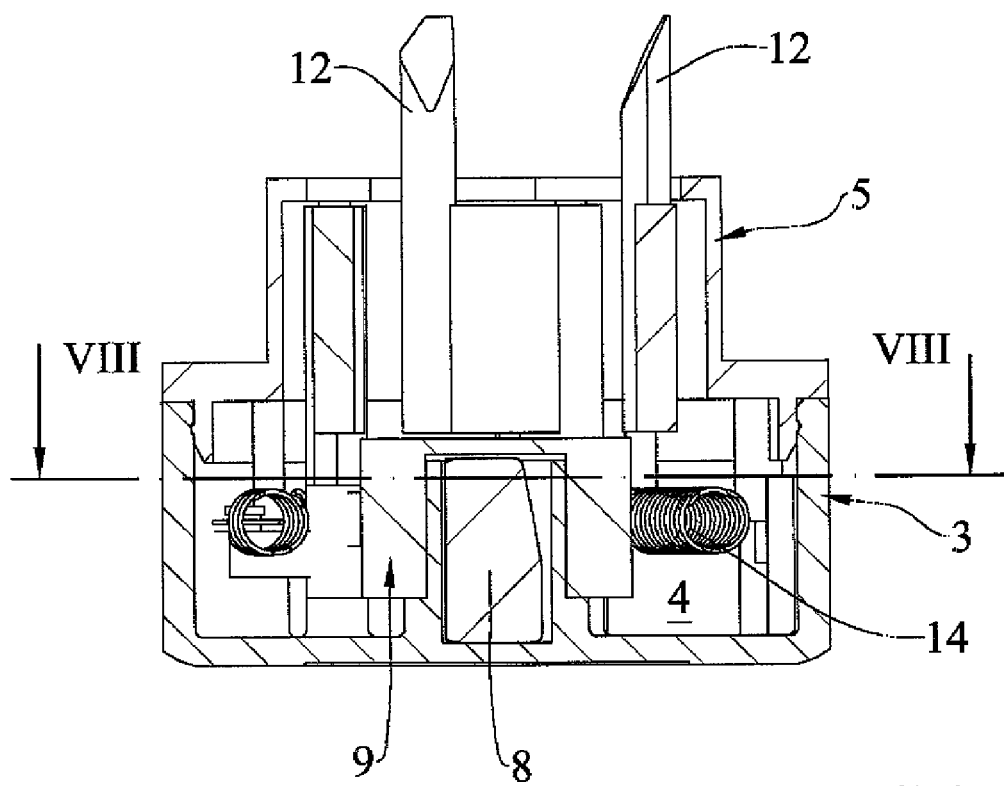
FIG. 3 is a sectional view according to line III-III of FIG. 2.

When a specimen container 2 is inserted into the carrier 1, the transversal size of the specimen container 2 forces the outward rotation (clockwise rotation of few degrees) of the fingers 12 (FIG. 2) and the reverse rotation (counterclockwise rotation) of the rotor 9.

The springs 14 continue to force the inward rotation of the fingers 12, so that the specimen container 2 is grasped by said fingers 12.

Each finger 12 acts the same inward force.

The specimen container 2 is hardly held in a vertical centred position.

The fingers 12 grasp the specimen container so that a wide portion of the external surface of said specimen container is visible; in this way the detecting sensors of the conveyor may always read the barcode of the specimen container 2 (see FIG. 1).

Moreover the portion of specimen container kept inside the fingers 12 is very limited and a huge portion of it remains available to allow gripping devices to access the specimen container for execution of process tasks (specimen container decapping, recapping and so on).

If the specimen container 2 is struck, the fingers 14 force the specimen container 2 to remain in the centered position.

It is possible to provide the fingers 12 with gear portions instead of single teeth, which engage with gear portions of the rotor 9.

The rotor 9 could also have a single external gear crown.

The invention claimed is:

1. A specimen container carrier for engaging a container on a conveyor in a laboratory automation system, comprising:

a base circular body having a plurality of pivoting holes, a plurality of spring coupling pintles, and a pin;

a closure member having a plurality of pivoting holes, wherein the base circular body and the closure member are attached to form a cavity;

a plurality of centering fingers, each finger including at least one tooth, a lower pivoting hinge operatively engaging the pivoting hole of the base circular body, and an upper pivoting hinge operatively engaging the pivoting hole of the closure member, and a spring coupling pintle, the fingers vertically extending over the base circular body;

a circular rotor provided with a plurality of slits and a rotor cavity rotatably mounted on the pin of the base circular body such that the circular rotor is disposed within the cavity; and a plurality of springs, each spring elastically connecting one of the plurality of fingers with the base circular body by coupling each base circular body pintle and the finger pintle, in order to provide an inward rotation of the fingers along the lower and upper hinges so that the container is grasped by the fingers, wherein the at least one tooth of the finger rotatably engages with the slit of the circular rotor in order to synchronize and balance the inward force of each finger, providing a centering action on the container.

2. The specimen container carrier according to claim 1, wherein the pin of the base circular body has a cavity in which a tag transponder is housed for identification of the specimen container carrier.

* * * * *